(12) United States Patent
Minton

(10) Patent No.: US 7,972,842 B2
(45) Date of Patent: Jul. 5, 2011

(54) LOCKABLE CELL GROWTH CHAMBER

(75) Inventor: Kenneth L. Minton, West Linn, OR (US)

(73) Assignee: PML Microbiologicals, Inc., Wilsonville, OR (US)

( * ) Notice: Subject to any disclaimer, the term of this patent is extended or adjusted under 35 U.S.C. 154(b) by 1884 days.

(21) Appl. No.: 11/112,671

(22) Filed: Apr. 21, 2005

(65) Prior Publication Data

US 2006/0240549 A1      Oct. 26, 2006

(51) Int. Cl.
*C12M 1/22* (2006.01)
(52) U.S. Cl. .................. 435/305.3; 435/297.5
(58) Field of Classification Search .............. 435/297.5, 435/305.4
See application file for complete search history.

(56) References Cited

U.S. PATENT DOCUMENTS

| | | | |
|---|---|---|---|
| 2,533,088 A | 4/1949 | Brewer et al. | |
| 2,677,647 A | 10/1952 | Lovell | |
| 3,158,553 A | 11/1964 | Carski | |
| 3,203,870 A | 8/1965 | Andelin | |
| 3,537,956 A | 11/1970 | Falcone et al. | |
| 4,634,676 A | 1/1987 | Sapatino | |
| 5,328,046 A * | 7/1994 | Kutz et al. ................ | 220/266 |
| 5,348,885 A * | 9/1994 | Labarthe ................ | 435/305.4 |
| 5,695,988 A | 12/1997 | Chong | |
| 6,602,704 B1 | 8/2003 | Maxwell et al. | |

FOREIGN PATENT DOCUMENTS

EP        0 171 174 A2    12/1986

* cited by examiner

*Primary Examiner* — William H Beisner
*Assistant Examiner* — Michael Hobbs
(74) *Attorney, Agent, or Firm* — Chernoff, Vilhauer, McClung & Stenzel

(57) ABSTRACT

A lockable cell growth chamber is disclosed wherein the lid and base of the dish are provided with at least two pairs of locking members, each comprising a notched docking member and a docking member-engaging tab.

10 Claims, 3 Drawing Sheets

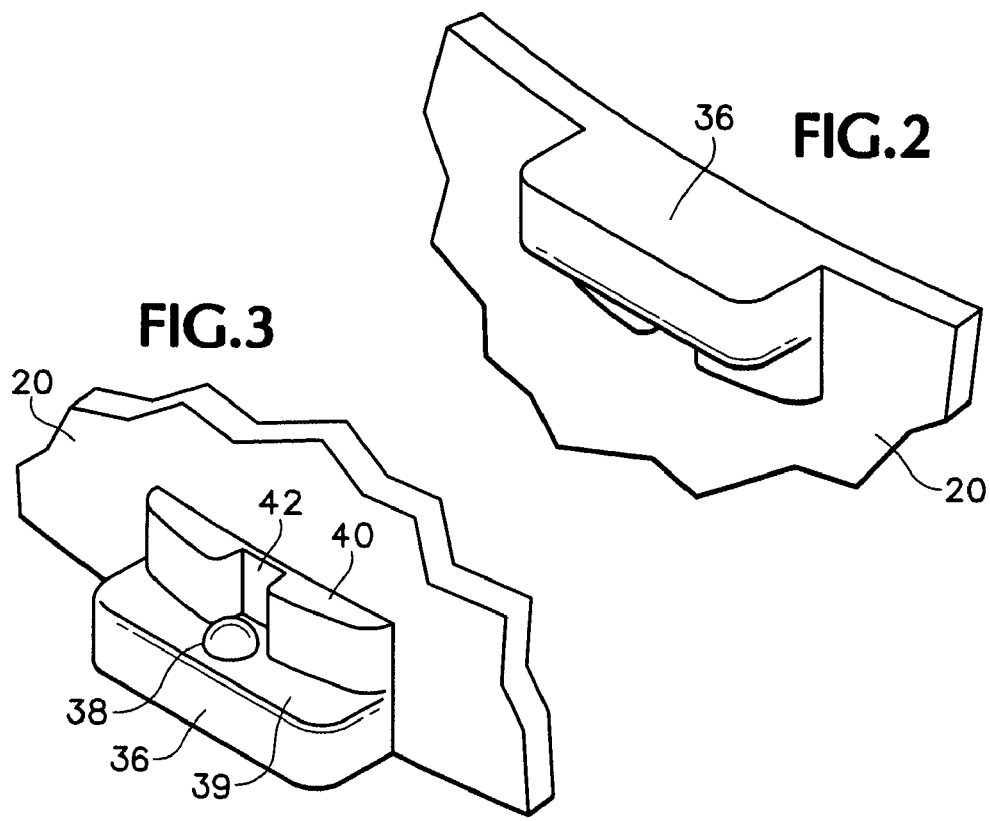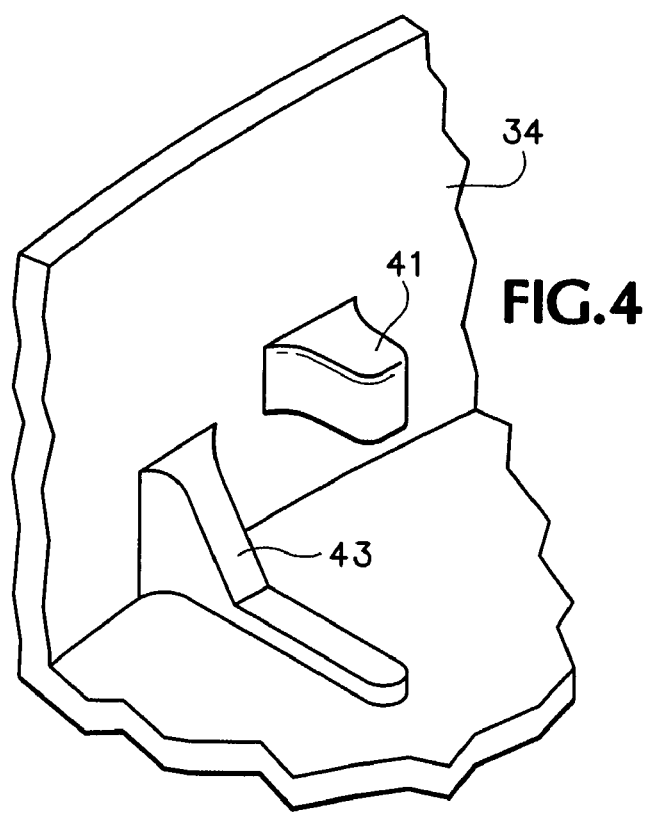

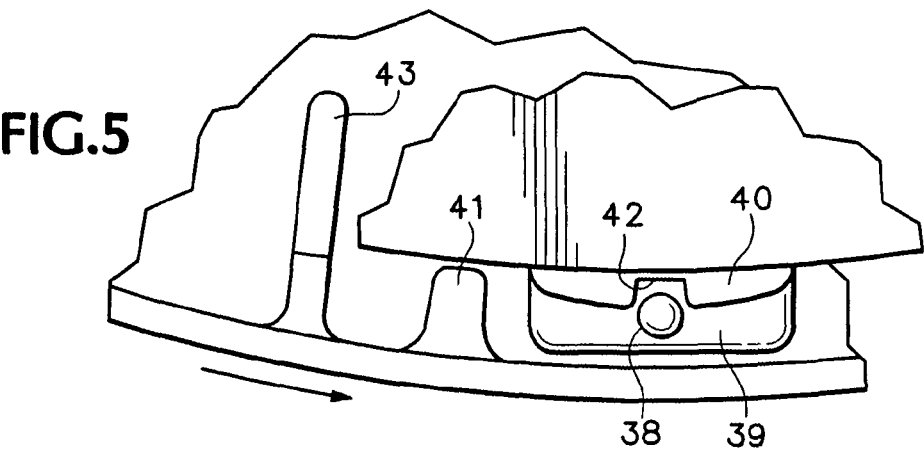
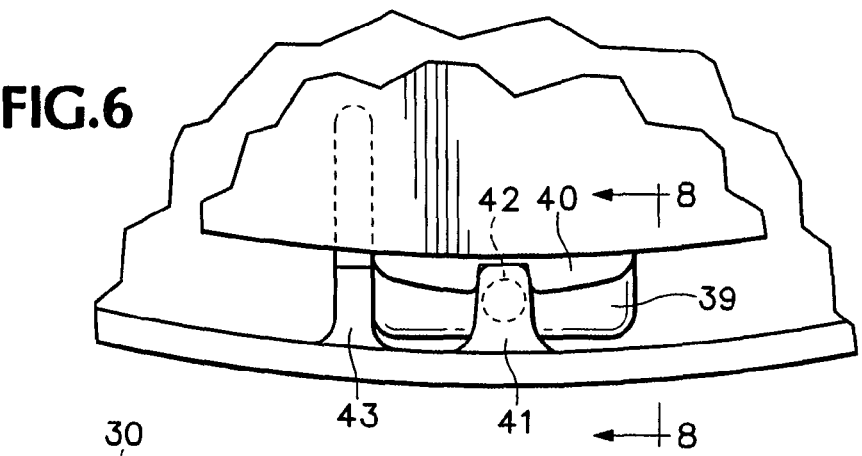
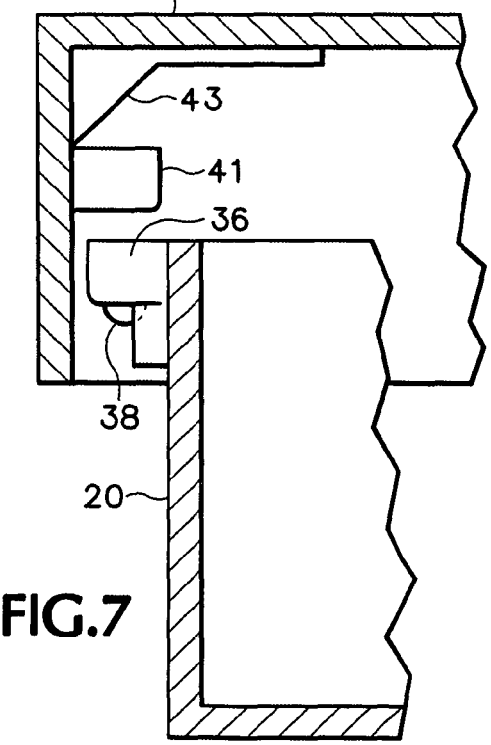
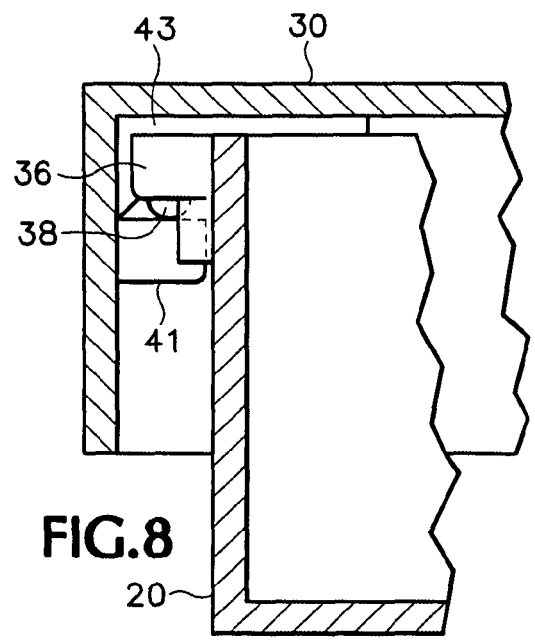

LOCKABLE CELL GROWTH CHAMBER

BACKGROUND OF THE INVENTION

The use of Petri dishes and contact plates for growing colonies of microorganisms such as bacteria or fungi is well known. A Petri dish typically comprises an open dish for holding microorganism growth medium and an overlapping cover that isolates the growth medium and microorganisms from the external environment. A contact plate is a much smaller version of a Petri dish, the dish component of which is pre-loaded with growth medium and is provided with a base for grasping the contact plate so as to permit it to be pressed against a surface to obtain a sample of any microorganism(s) present on the sampled surface.

Petri dish covers may be loosely fitting so that the seal on the dish arises simply from the weight of the cover bearing upon the cylindrical side walls of the dish. Petri dish covers may also be tightly securable to and detachable from the dish, which prevents opening of the Petri dish when it is accidentally bumped or knocked over. One such Petri dish design is disclosed in U.S. Pat. No. 3,769,936, wherein the cover may be secured to the dish by ribs in the side walls of the cover that resiliently contact the side walls of the dish so as to form a compression fit. However, this design has the inherent drawback that the compression fit is often either too tight to allow ready disengagement between the cover and dish or too loose, which can lead to accidental spillage or contamination when handling the Petri dish.

Contact plates are typically fabricated from polymeric material in mass quantities at a sufficiently low cost as to be disposable after a single use. The dish portion of the contact plate is filled with a generally convex mound of growth medium. With the lid removed, the contact plate is grasped by its base and the mound of growth medium is pressed against a surface to be tested for bacterial and/or fungal contamination. The lid is then replaced and the contact plate is stored in an environment conducive to microorganism growth. A typical contact plate is pre-loaded with growth medium under sterile conditions and packaged for shipment to the end user.

Two known designs of contact plates are those that are the subject of U.S. Pat. Nos. 5,854,065 and 6,602,704. Both designs have the inherent drawback that the lid and base are held together by a compression fit that is often either too tight to allow ready disengagement between the lid and base or too loose, which can lead to accidental spillage or contamination when handling the contact plate. Another contact plate design is the subject of commonly assigned U.S. application Ser. No. 10/695,066, filed Oct. 27, 2003, now U.S. Pat. No. 6,969,606 which discloses a lockable contact plate wherein the locking members consist of pairs of radial sheaths and tabs.

What is needed therefore are a lockable Petri dish and a lockable contact plate that do not lock except upon application of a specific intentionally applied force, that provide a secure locking engagement between the cover and the dish, and which may be readily disengaged from the locking engagement. These needs are met by the present invention, which is summarized and described in detail below.

BRIEF SUMMARY OF THE INVENTION

The present invention comprises a lockable cell growth chamber that may be in the form of a Petri dish or a contact plate wherein the cover and dish components are prevented from premature or accidental locking engagement with each other so as to permit rapid pre-loading with growth medium, yet are readily lockable and unlockable from each other.

The foregoing and other objectives, features, and advantages of the invention will be more readily understood upon consideration of the following detailed description of the invention taken in conjunction with the accompanying drawings.

BRIEF DESCRIPTION OF THE VIEWS OF THE SEVERAL DRAWINGS

FIG. 2 is a partial perspective view of one of the two locking members.

FIG. 3 is a partial perspective view of the underside of the locking member shown in FIG. 2.

FIG. 4 is a partial perspective view of the other of two locking members.

FIG. 5 is a cutaway view of the two locking members prior to locking engagement.

FIG. 6 is a cutaway view of the two locking members after locking engagement.

FIG. 7 is a cross-sectional view of the cell growth chamber of the invention in the vicinity of a pair of locking members with the lid shown as being raised from the dish.

FIG. 8 is a cross-sectional view of FIG. 6 taken through the plane 8-8.

DETAILED DESCRIPTION OF PREFERRED EMBODIMENTS

Figure 1:
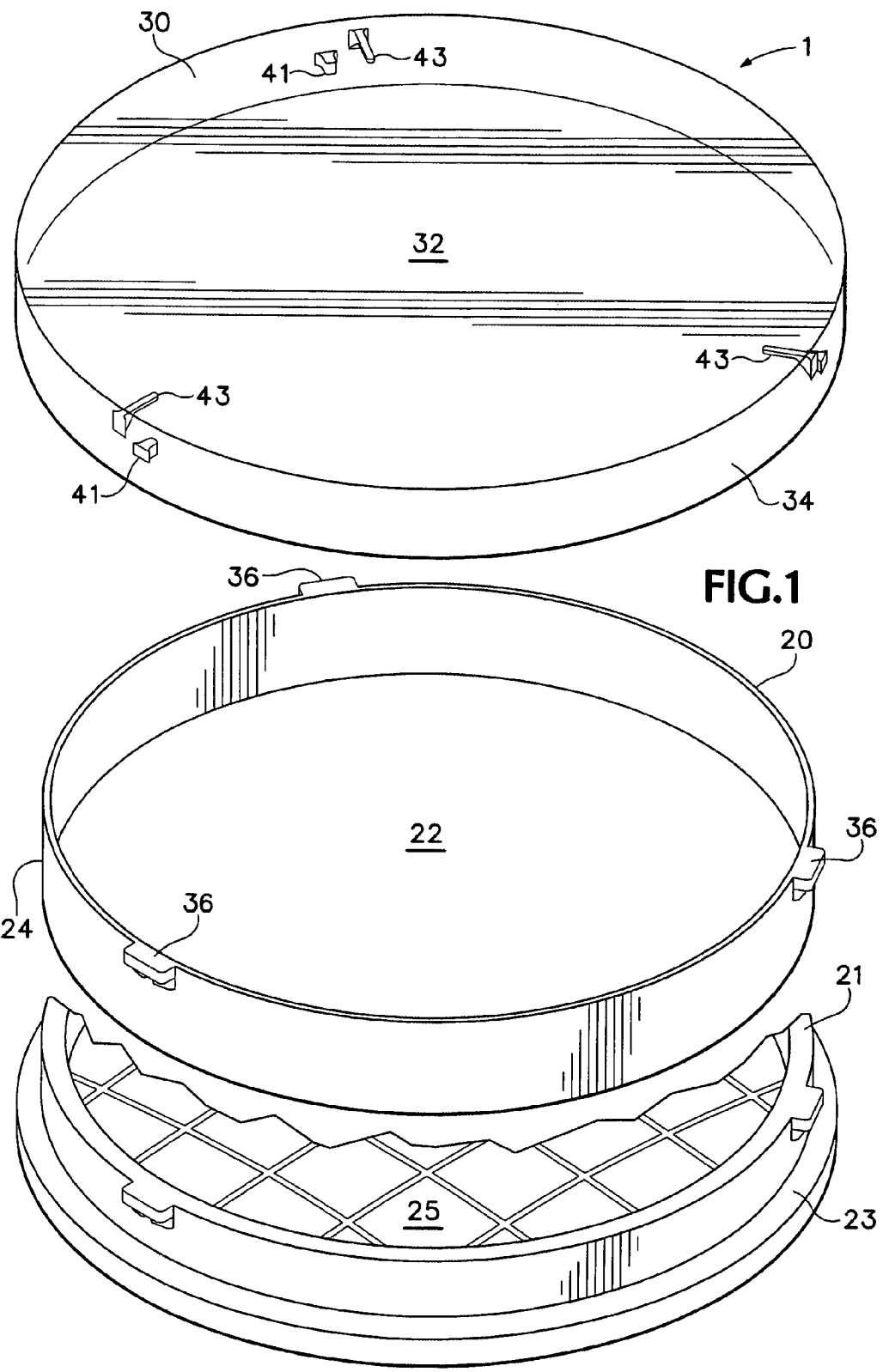
FIG. 1 is an exploded perspective view of two exemplary embodiments of the lockable cell growth chamber of the invention.

Referring to the drawings, wherein the same numerals refer to like elements, there is shown in FIGS. 1-8 a cell growth chamber 1 comprising a circular dish 20, dish 20 consisting of a flat bottom plate 22 and a bottom cylindrical sidewall 24. The cell growth chamber further comprises a circular lid 30, consisting of a lid top plate 32 and a top cylindrical side wall 34. Lid 30 is preferably transparent so as to permit viewing of any microorganism growth. Dish 20 may be provided with a flange 23 around its base when the function of the cell growth chamber is to serve as a contact plate; in such a case flange 23 serves as a handle for gripping and manipulating the cell growth chamber so that it can be readily pressed against a surface to be sampled for the presence of microorganisms.

Dish 20 and lid 30 are provided with locking means for securing the base and lid in locking engagement. The locking means comprises at least two pairs of locking members radially spaced apart from each other, preferably equidistantly, wherein each pair of locking members comprises docking and tab members adapted to slidably and compressionably register with each other. More specifically, docking member 36 is preferably integral with bottom cylindrical side wall 24 of dish 20 and consists of land 38 preferably in the form of a hemispherical bead, platform 39 and ramp 40 having a notch 42 therein, all best seen in FIGS. 2-3 and 5. The inside of top cylindrical side wall 34 is provided with tab 41 situated so as to be in registry with land 38 and notch 42 of docking member 36 when dish 20 and lid 30 are in the locked position. Although docking member 36 and tab 41 are preferably integral with dish 20 and lid 30, respectively, it should be understood that this arrangement could be reversed and still yield the desired locking means of the invention.

Preferably all parts of the cell growth chamber are fabricated from a polymeric material having a slight degree of resiliency. A preferable polymeric material is polystyrene.

To engage the locking arrangement, lid 30 is placed over dish 20 so that tabs 41 are proximate to docking members 36, best seen in FIG. 5, then dish 20 is rotated relative to lid 30 (shown by the directional arrow in FIG. 5), or vice-versa, until tabs 41 engage platforms 39 and ramps 40. Rotation is continued until tabs 41 engage lands 38 and notches 42 and stops 43 engage the proximal walls of docking members 36. Because all of the parts of the cell growth chamber are made of polymer having a degree of resiliency, during the locking step, both top cylindrical side wall 34 and bottom cylindrical side wall 24 distort slightly as tabs 41 are forced up ramps 40, then snap back to their original round configuration as tabs 41 snap into registry with lands 38 and notches 42. At the same time, tabs 41 and lands 38 resiliently yield to each other. Thus, the combination of slight side wall distortion and mutual yielding of the tabs and lands assures a snug compression fit between tabs 41 and docking members 36. Stops 43 prevent tabs 41 from overriding notches 42 in the event an excessive torquing force is applied. Once dish 20 and lid 30 are in locking engagement, accidental removal of the lid from the base is prevented.

It is often advantageous to pre-load dish 20 with a growth medium such as agar or a gel containing microorganism-specific nutrients or indicators, then assemble the base and lid components, seal them in sterile packaging and ship them to the laboratory or other end user. Such a pre-loaded dish is depicted in the lower portion of FIG. 1, which shows growth medium 25 having a grid superimposed thereon to facilitate microorganism colony counting and to otherwise track cell growth. Such pre-loading and prepackaging is typically conducted on an automated basis, assembly-line style, with the lids rapidly being removed and replaced on the dishes by a mechanical arm immediately before and after the agar or gel pour. For speed and efficiency, it is best that, immediately before and after the loading, the lid not enter into locking engagement with the dish as this tends to interfere with and slow down the automated pre-loading process. To prevent premature locking engagement between dish 20 and lid 30 on such a pre-loading assembly line, tabs 41 engage ramps 40 which, absent the application of a torquing force to lid 30 (or to dish 20), prevents entry of tabs 41 into notches 42 of docking members 36.

The cell growth chamber of the invention containing growth medium is preferably manufactured in an unlocked arrangement and is packaged for shipment to the end user in gas-impermeable sterile packaging.

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

I claim:

1. A lockable cell growth chamber comprising
(a) a circular dish supported on a circular base, said dish having a bottom plate and a bottom cylindrical side wall, and
(b) a circular lid having a top plate and a top cylindrical side wall, said lid sized so as to fit over the bottom cylindrical side wall of said dish wherein said base and said lid are provided with locking means for securing said base and lid in locking engagement, said locking means comprising at least two pairs of locking members, each of said pairs of locking members comprising (i) a docking member having a notch and a ramp, and (ii) a tab sized and shaped so as to be slidably and compressionably engagable with said notch of said docking member, and wherein said docking member includes a platform that is substantially at right angles to said ramp, said top cylindrical side wall includes a stop adjacent each tab, and said stop is located and shaped so as to engage one side of said docking member when said tab is within said notch.

2. The cell growth chamber of claim 1 wherein said docking member is integral with said bottom cylindrical side wall and said tab is integral with said lid.

3. The cell growth chamber of claim 2 wherein said docking member has a land in the vicinity of said notch that is sized and located so as to be matingly engagable with said tab.

4. The cell growth chamber of claim 3 wherein said docking member includes a ramp and said notch is substantially centered in said ramp.

5. The cell growth chamber of claim 1 wherein said docking member and said tab are slidably engagable with each other by rotating said lid relative to said base.

6. The cell growth chamber of claim 5 wherein said docking member and said tab are slidably disengagable from each other by rotating said lid relative to said base.

7. The cell growth chamber of claim 1 wherein said lid is transparent.

8. The cell growth chamber of claim 1 wherein said base has a circumferential flange.

9. The cell growth chamber of claim 1 wherein said dish contains microorganism growth medium.

10. The cell growth chamber of claim 9 packaged in sterile packaging.

* * * * *